US005480401A

United States Patent [19]

Navas

[11] Patent Number: 5,480,401
[45] Date of Patent: Jan. 2, 1996

[54] EXTRA-DISCAL INTER-VERTEBRAL PROSTHESIS FOR CONTROLLING THE VARIATIONS OF THE INTER-VERTEBRAL DISTANCE BY MEANS OF A DOUBLE DAMPER

[75] Inventor: Fernand Navas, Charbonnieres-les-Bains, France

[73] Assignee: PSI, Lyons, France

[21] Appl. No.: 194,276

[22] Filed: Feb. 10, 1994

[30] Foreign Application Priority Data

Feb. 17, 1993 [FR] France ................................. 93 02184
May 17, 1993 [FR] France ................................. 93 06174

[51] Int. Cl.⁶ ............................... A61B 17/70; A61F 2/44
[52] U.S. Cl. ................... 606/61; 623/17; 403/137; 267/153; 267/195
[58] Field of Search .................. 606/61; 623/17; 403/137, 138, 135, 144; 267/292, 153, 195, 141

[56] References Cited

U.S. PATENT DOCUMENTS 4,932,975   6/1990   Main et al. ............................. 606/61

FOREIGN PATENT DOCUMENTS

0516567   5/1992   European Pat. Off. ............... 606/61

Primary Examiner—Stephen C. Pellegrino
Assistant Examiner—Scott B. Markow
Attorney, Agent, or Firm—Dowell & Dowell

[57] ABSTRACT

A prosthesis with double damper performing the function of intervertebral stabilizer which comprises at least two identical elements assembled together and comprising elastic bodies for regulating the bending-stretching movement between two vertebrae so as to approach as closely as possible the physiological course of a discal movement.

25 Claims, 7 Drawing Sheets

EXTRA-DISCAL INTER-VERTEBRAL PROSTHESIS FOR CONTROLLING THE VARIATIONS OF THE INTER-VERTEBRAL DISTANCE BY MEANS OF A DOUBLE DAMPER

BACKGROUND OF THE INVENTION

1. Field of the Invention

The present invention relates to a prosthesis with double damper, allowing the function of intervertebral stabilizer by controlling the interpedicular distance.

2. History or the Related Art

Dampers of this type are known, which are generally with single or double effect and which may progressively resist, in exponential manner, the advance of a piston, so that, after a certain stroke of the piston, the damper opposes any displacement of the piston beyond a determined value. To that end, the damper contains on either side of the piston an elastic body whose volume is smaller than that of the chamber determined by the position of the piston in the free state with respect to the bottom of the cylinder.

The variation of the volume of the chamber or of the compartment brings about a deformation of the corresponding elastic body which is opposed by the non-deformability of the walls of the chamber, so that a resistive force progressively opposes the displacement of the piston until it stops when this force becomes exponential.

The improvements forming the subject matter of the present invention allow a damper to be produced, comprising two identical, separate elements assembled together and comprising means for regulating the bending-stretching movement between two vertebrae, by developing an exponential curve in the two directions so as to approach as much as possible the physiological course of a discal movement.

SUMMARY OF THE INVENTION

Each element comprises a hollow cylinder provided with an opening and having one of its ends closed by a bottom wall with a tenon extending therefrom, while the other end receives a disc which, via an assembly ring, allows the connection with another element. A sleeve placed is the cylinder and has one of its ends closed by a bottom while the other receives a face of the disc on which. A boss is provided, a notch is made on the periphery of the sleeve. A screw having a spherical head is mounted to pivot between the disc and the bottom of the sleeve and an elastic body is placed between the sleeve and the bottom of the cylinder so as to dampen the displacements thereof under the effect of the displacements of the screw.

A variant embodiment consists in that, for each element, at least one cylinder is provided, of which one of the ends is closed by a bottom, while the other end comprises an assembly ring which allows connection with another element. The median part of the cylinders are provided with a transverse hole for positioning a tubular sleeve provided to receive by force a sphere of a pedicular screw. Between each sleeve and the bottom, there is placed an elastic body while another elastic body is introduced between each sleeve and the assembly ring.

Moreover, each sleeve is elastically maintained in the axial direction of the cylinders, the displacements of the sleeve in one direction or in the another being effected against the reaction of the corresponding elastic body.

BRIEF DESCRIPTION OF THE DRAWINGS

The invention will be more readily understood on reading the following description with reference to the accompanying drawings, in which.

DESCRIPTION OF PREFERRED EMBODIMENTS

Figure 1:
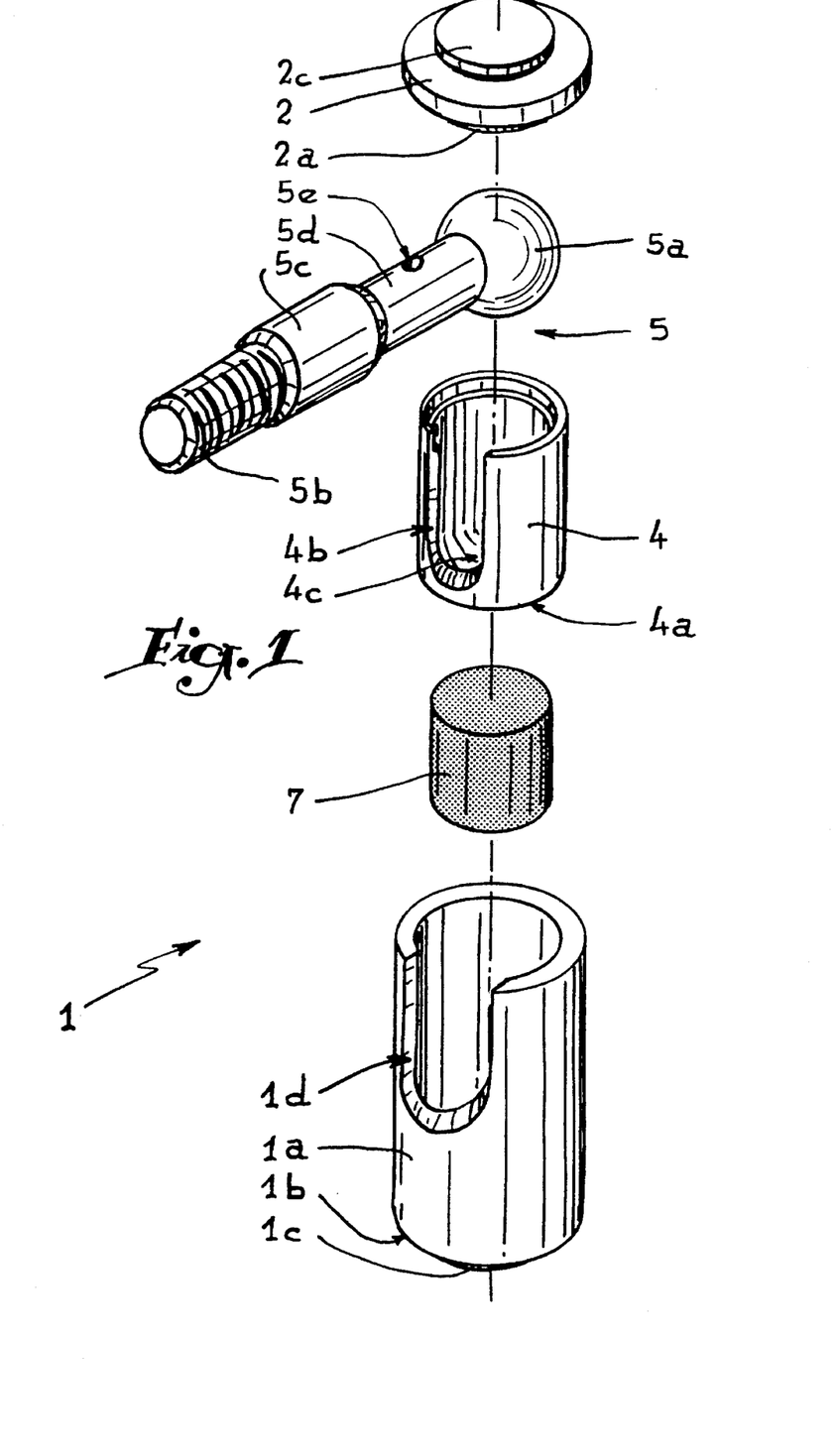
FIG. 1 is an exploded view in perspective showing an element of the damper according to the present invention.

Referring now to the drawings, FIG. 1 firstly shows an isolated element 1 which is to be assembled with another, identical element, to constitute the intervertebral damper according to the invention.

Each element 1 comprises a hollow cylinder or body 1a of which one of the ends is closed by a bottom 1b, while the other, which is open, is intended to receive a disc 2. The outer face of the bottom 1b is machined to constitute a T-tenon 1c which allows connection with an assembly ring 3, as will be seen more clearly hereinafter.

Figure 3:
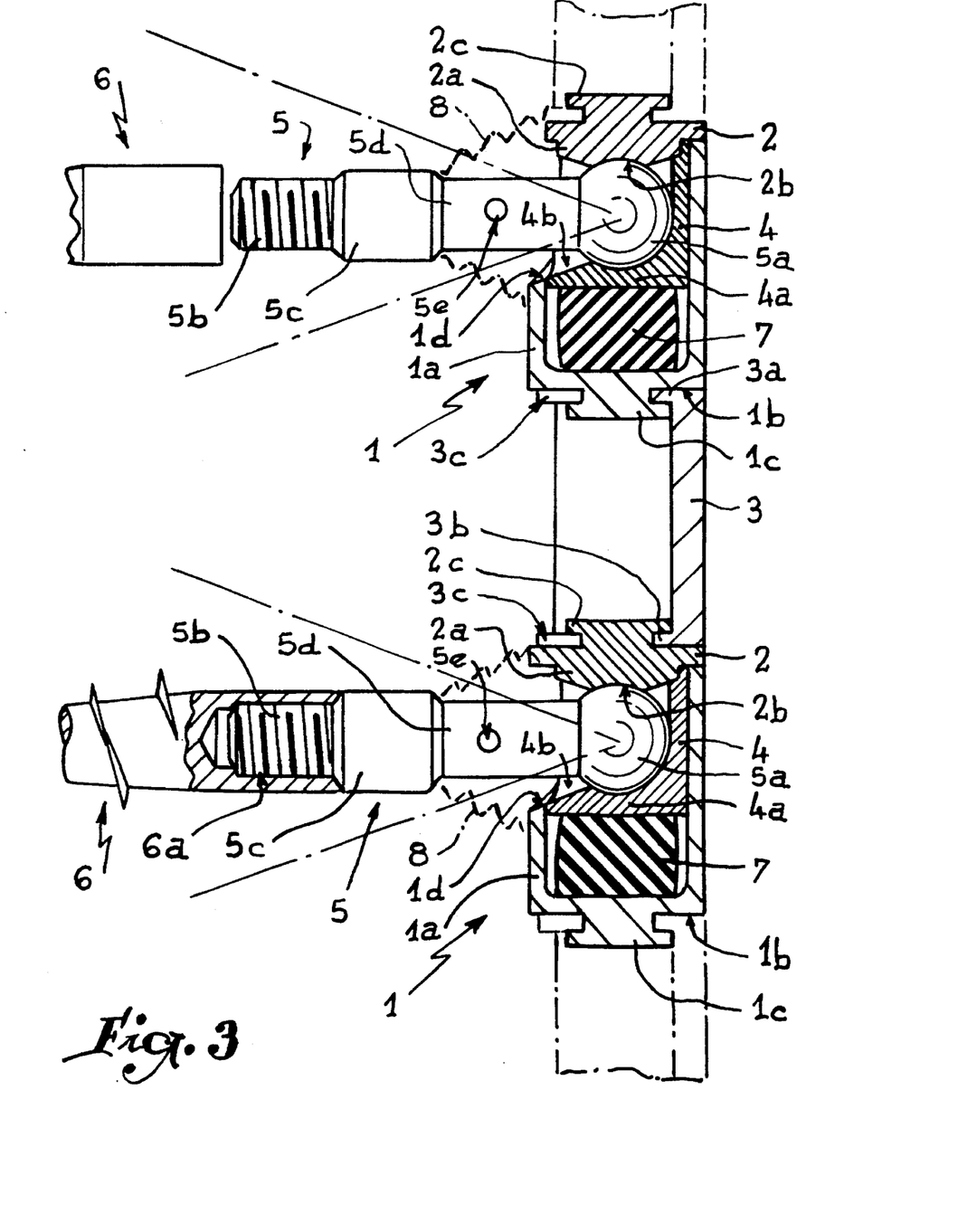
FIG. 3 is a section showing the damper provided with two elements of FIG. 1 joined by means of an assembly ring to perform the function of intervertebral stabilizer.

Cylinder 1a is provided with a slot or longitudinal opening 1d which opens out towards the end which is to receive the disc 2. This latter comprises on one of its faces a boss 2a whose center is machined to constitute a hollow 2b of a shape corresponding to part of a sphere, as shown in FIG. 3. Disc 2 comprises on the face opposite the one comprising the boss 2a, a projection 2c in the form of a tenon identical to that, 1c, provided on the bottom 1b of the cylinder 1a.

A tubular sleeve 4 is closed at one of its ends by a bottom 4a, while the other is open in order to receive the boss 2a of the disc 2 when the element 1 is mounted. The periphery of the sleeve 4 is provided with a longitudinal notch 4b which opens out towards the end receiving the boss 2a. The inner part of the bottom 4a is machined to determine a hollow 4c of radius identical to that, 2b, provided in the boss 2a of disc 2. The element 1 further comprises a pivotable connector for a pedicular screw which consists of a screw 5 of which one of the ends comprises a sphere 5a whose radius corresponds to that of the hollows. The screw 5 comprises, opposite sphere 5a, a threaded part 5b which allows fixation thereof in a pedicular screw 6, as will be seen more clearly hereinafter. Between the threaded part 5b and the sphere 5a, the screw 5 is provided with a bearing surface 5c and with a smooth cylindrical part 5d which is pierced right through with a transverse hole 5e. It will be observed that the diameter of part 5d is smaller than that of the bearing surface 5c.

Between the bottom 4a of the sleeve 4 and the bottom 1b of the cylinder 1a, there is placed an elastic body 7 such as a block of natural or synthetic rubber. The volume of the elastic body 7 in the free state is slightly smaller than that of the chamber in which it is placed which is determined by the inner volume of the cylinder 1a defined between its bottom 1b and the sleeve 4. The sleeve 4 is introduced in the cylinder 1a so that its notch 4b is placed opposite that, 1d, of the cylinder. The head 5a of the screw 5 is then introduced inside the sleeve 4 so that the smooth part 5d passes through the notches 1d and 4b.

The disc 2 which closes the sleeve and the element 1 is welded on the periphery of the cylinder 1a so that its boss 2a is placed inside the sleeve 4. It will be noted that the hollow 2b of the boss 2a comes into abutment against the sphere 5a of the screw 5 to guide it pivotably inside the sleeve 4.

Figure 2:
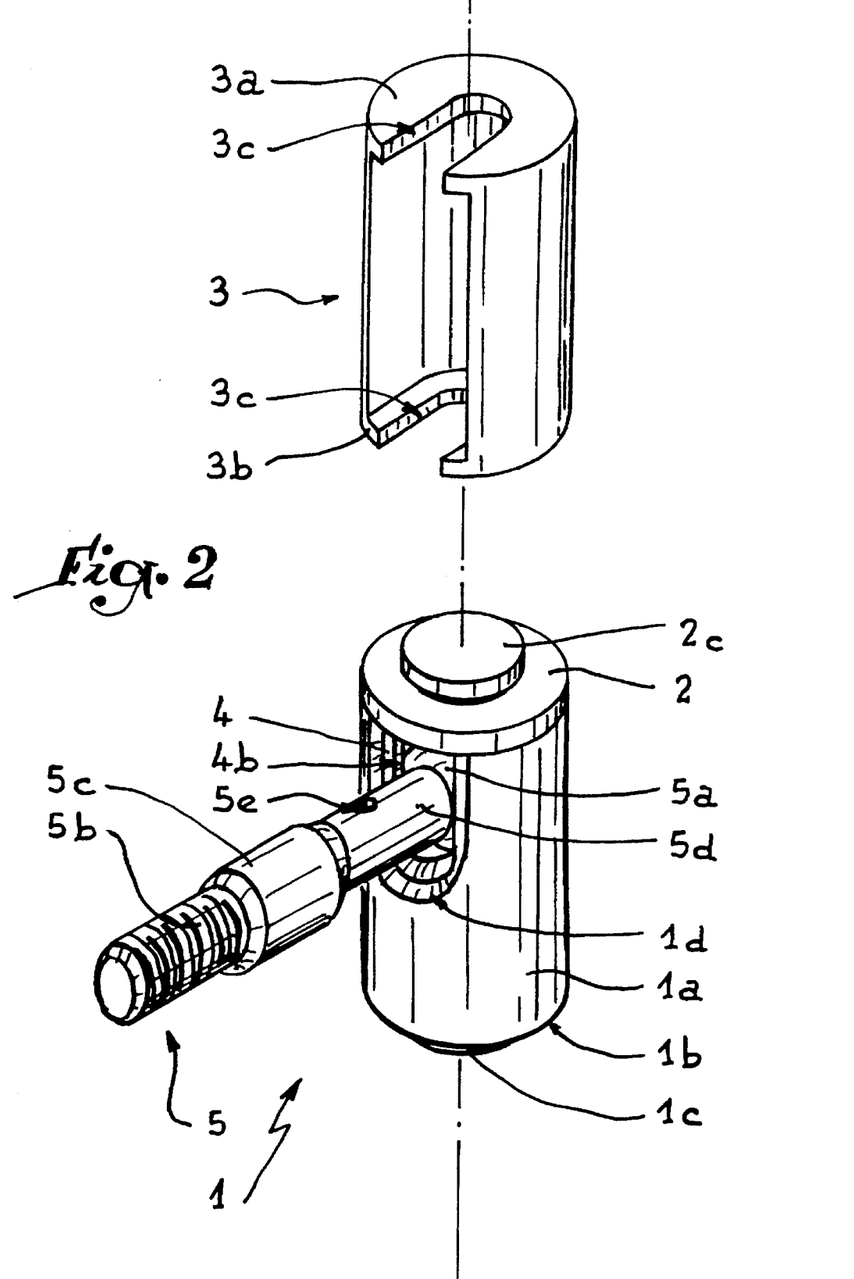
FIG. 2 is a view in perspective showing the element mounted, on which is clipped an assembly ring for connection with another element.

FIG. 2 shows an element 1 completely assembled, on which is engaged the assembly ring 3. The latter makes it possible to join two identical elements 1 to constitute the damper according to the present invention. The ring 3 has a hollow, cylindrical profile of which the ends are closed by parallel end walls 3a and 3b which are each provided with a notch 3c whose diameter is slightly smaller than that of the tenons 1c and 2c provided respectively on the cylinder 1a and on the disc 2. The ring 3 may be totally rigid or supple or articulated so that the elements 1 may pivot with respect to one another.

FIG. 3 shows two elements 1 described hereinabove and assembled with one another by means of the ring 3 with a view to constituting the damper. Each of the screws 5 is fixed in a pedicular screw 6 previously screwed in the body of two vertebrae to be stabilized. Each pedicular screw 6 presents at one of its ends a threaded tapped hole 6a in which is screwed the threaded part of the screws 5. The screws 5 may also be fixed by any other means inside the pedicular screws 6. Around each screw 5, there is provided a bellows 8 which surrounds the smooth part 5d and which abuts on the boss 5c and on the outer face of the cylinder 1a. The bellows are compressed at the moment of assembly so that the notches 1b and 4b are never to particles such as blood or flesh, which would risk blocking the angular displacements of the damper.

It will be noted that the elements 1 are mounted in the same direction so that the ring 3 cooperates, on the one hand, with the first element by means of the tenon 2c and, on the other hand, with the second element via the tenon 1c. This particular arrangement makes it possible to stabilize and dampen the displacements of the vertebrae either in traction or in compression.

Figure 4:
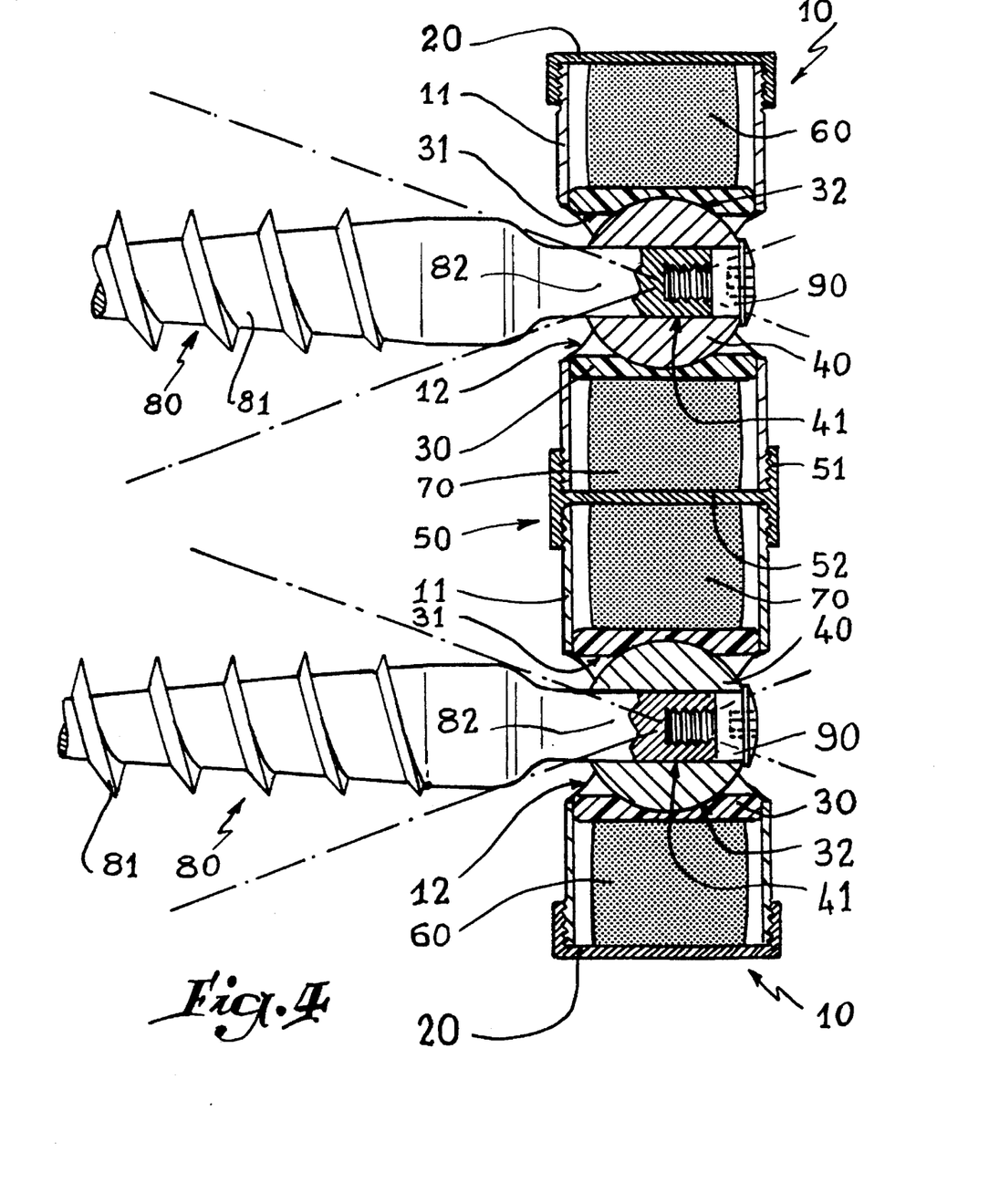
FIG. 4 is a view illustrating a first variant of the damper according to the invention.

FIG. 4 shows a first variant of the damper according to the invention which comprises two identical elements 10 assembled together.

Each element comprises a cylinder or body 11 open at its two ends and of which one is closed by a bottom 20, preferably screwed, but which may be fixed by any other means.

The median part of the cylinder 10 is provided with a transverse through hole 12 in which is engaged a tubular sleeve 30 or piston. The tubular sleeve 30 is made either of metal or of an appropriate plastic material such as polyethylene. It has a bore 31 comprising in its median part a hollow 32 whose shape corresponds to a part of a sphere. In this hollow 32 is engaged a sphere 40, for pivotably connecting a pedicular screw within the sleeve, whose radius may correspond to or be more widened than that of the hollow.

The two cylinders 11 are assembled by means of a ring 50 constituted by a cylindrical collar 51 whose ends are respectively screwed on the two opposite, adjacent ends of the two cylinders 11. It will be observed that the ring 50 is provided with a median transverse wall 52 whose thickness may vary depending on the use of the damper and which constitutes a partition separating the cylinders 11. This partition 11 may also be either articulated or flexible.

Between each sleeve 30 and the bottom 20 of the corresponding cylinder is placed an elastic body 60 such as a block of natural or synthetic rubber. The volume of the elastic body 60 in the free state is slightly smaller than that of the chamber in which it is placed and which is determined by the inner volume of the cylinder 11 defined between its bottom 20 and the sleeve 30. Another elastic body 70, identical to body 60, is placed between each sleeve 30 and the separating partition 52 of the assembly ring 50.

In this way, each sleeve 30 is maintained elastically in the axial direction of the cylinder 11, the displacements of the sleeve in one direction or in the other being effected against the elastic reaction of the corresponding body.

With a view to the application of the damper described hereinabove to the stabilization of two adjacent vertebrae of a spine, in each sphere 40 has a radial hole 42 in which is introduced a cylindrical end 82 of a pedicular screw 80. In fact, the pedicular screw 80 is anchored in the apophysis of a vertebra by its threaded end 81, while its other cylindrical end 82 is associated with a bore 41 of the sphere 40 via a screw 90. The screw 90 comprises a head which has a larger diameter than that of the cylindrical part 82, so as to constitute a stop preventing separation of the sphere 40 and the screw 80, while allowing the latter to move longitudinally in the bore 41.

Of course, the transverse hole 12 of each cylinder 11 allows the pedicular screw 80 to be associated with the corresponding sphere 40.

Figure 5:
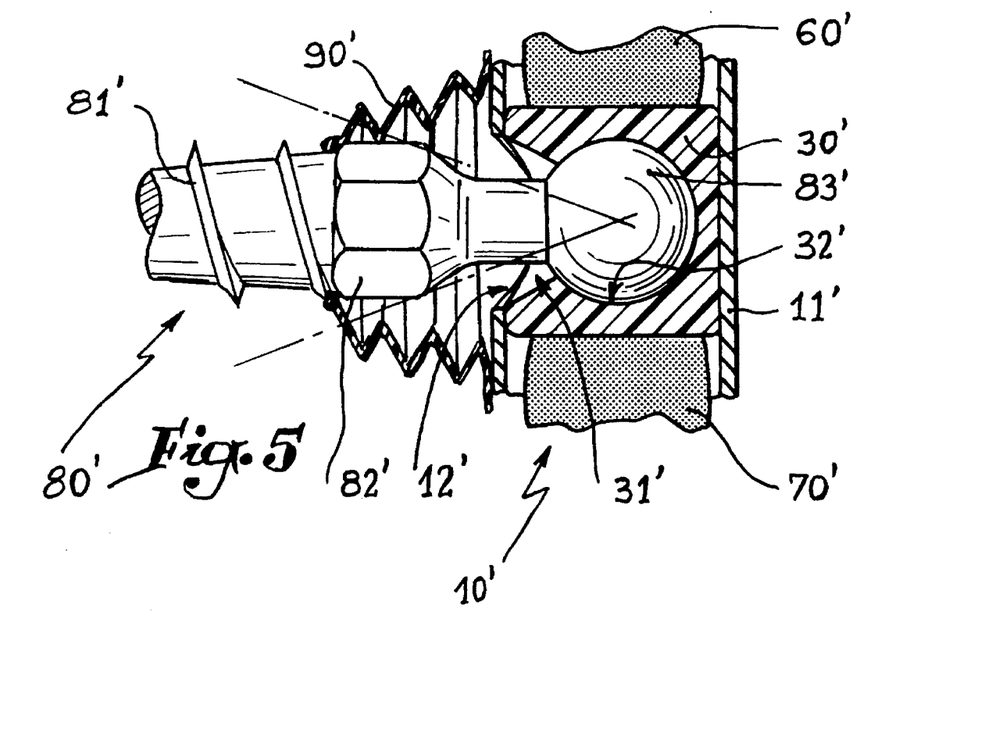
FIG. 5 is a view showing a second variant of the damper for positioning thereof on particular pedicular screws.

FIG. 5 shows a second variant of the damper so that it may be mounted on particular pedicular screws 80'.

The damper comprises two identical elements 10' each provided with a cylinder or body 11' open at its two ends and of which one is closed by a bottom (not shown), identical to the one referenced 20 (FIG. 4).

In the median part of the cylinder 11' is a transverse, non-opening hole 12'. In the cylinder 11' there is engaged a tubular sleeve 30' which is made of an appropriate plastics material such as polyethylene. The sleeve 30' comprises a bore 31' of conical profile whose wider base is turned towards the outside of the sleeve. The bore 31' opens out in a cavity 32' in the form of a sphere.

On either side of the sleeve 30' are provided two elastic blocks 60' and 70', identical to those described in the damper of FIG. 4. The pedicular screw 80' comprises a threaded part 81' which allows anchoring thereof in the apophysis of a vertebra. The wider base of the threaded part 81' is secured to a hexagonal profile part 82' which is extended along the major axis of the screw 80' by a spherical head 83' whose radius corresponds to that of the cavity 32' of the sleeve 30'.

The hexagonal profile part 82' enables the operator to screw the pedicular screw 80' in the apophysis of the vertebra to be stabilized. Once the pedicular screw 80' is anchored in the apophysis, its spherical head 83' is engaged by force in the cavity 32' of the sleeve 30'. It will be observed that, prior to positioning the damper on the spherical head 83' of the pedicular screw 80', a bellows 90' is placed which surrounds the hexagonal part 82' and which abuts on the outer face of the cylinder 11'. The bellows 90' is compressed at the moment of assembly so that the bore 12' is never in contact with blood or flesh which would risk blocking the angular displacements of the damper.

Functioning is as follows: two pedicular screws 6 or 80 or 80' being anchored in two adjacent vertebrae whose common disc is damaged, there is obtained thanks to the damper according to the invention, a damping of the relative movement of the two vertebrae in extension and in bending.

In fact, if the two pedicular screws 6 or 80 or 80' tend to move apart, which provokes a spacing apart of the two spheres 5a or 40 or 83', the block 7 of the element 1 being located in the lower part of the damper or the two blocks 60 and 60 are compressed and are deformed. However, the deformation is countered by the rigidity of the walls of each cylinder 1a or 11 or 11' so that the elastic block opposes the displacement of the sleeve 4 or 30 or 30' with an increasing reaction. When the sleeve 4 or 30 or 30' occupies the whole volume of the chamber in which it is disposed, the reaction developed by this block becomes exponential and at the limit, forms a stop preventing any subsequent displacement of the sleeve 4 or 30 or 30'. Consequently, the intervertebral displacement is limited.

The same applies when the two spheres 5a or 40 or 83' tend to approach one another. At that moment, the same phenomenon is produced as the one described herein-above, but which is resisted by to the block 7 of the element 1 located in the upper part of the damper or to the two blocks 70 or 70'.

Figure 6:
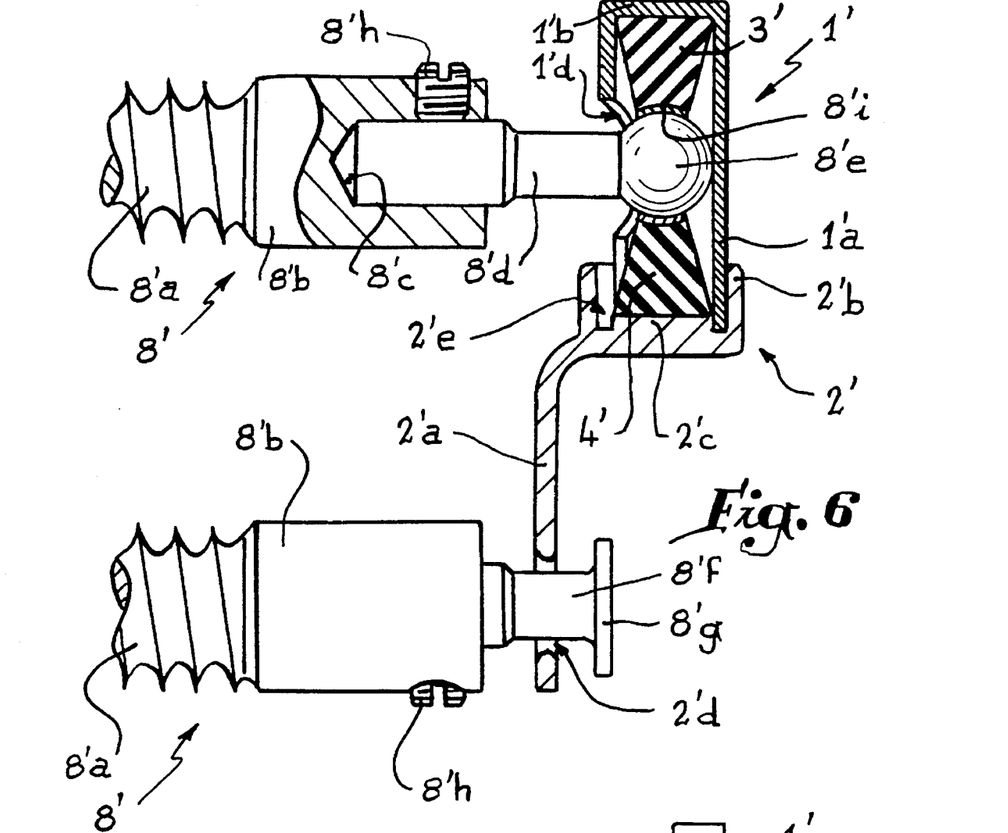
FIG. 6 is a view illustrating a third variant of the damper according to the invention.
Figure 7:
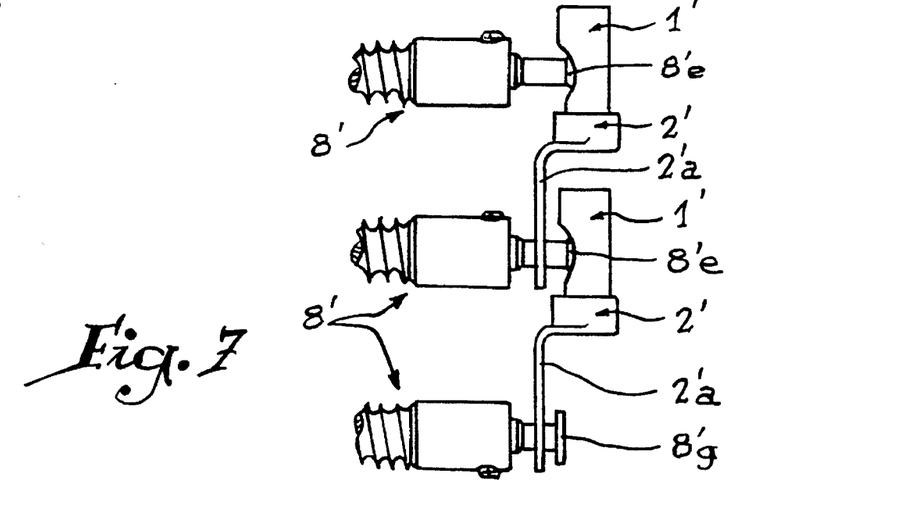
FIG. 7 is a schematic view showing the positioning of a plurality of dampers shown in FIG. 6.

FIGS. 6 and 7 show a third variant of the damper according to the invention which comprises an element 1' mounted on pedicular screws 8' previously anchored in the vertebrae.

Element 1' comprises a hollow cylinder or a body 1'a of which one of the ends is closed by a bottom 1'b, while the other, which is open, is intended to receive a disc 2' secured to a fixing lug 2'a which is provided at its free end with a hole 2'd. The lug 2'a is provided to be laterally offset with respect to the middle of the disc 2' in order to be in a plane parallel to the one passing through the vertical axis of the element 1'.

The cylinder 1'a has a longitudinal slot or notch 1'd which opens out towards the end which is to receive the disc 2'. The latter comprises a skirt 2'b extending vertically so as to guide the hollow cylinder 1'a axially. Between the walls of the skirt 2'b there is provided a bearing surface 2'c of cylindrical form and whose diameter is substantially equivalent to the internal diameter of the cylinder 1'a. The skirt 2'b and the bearing surface 2'b define a notch 2'e in which is introduced the open end of the hollow cylinder 1'a with a view to cooperating with the disc 2'.

The pedicular screws 8' anchored in the vertebrae of the spine comprise a self-tapping threaded part 8'a and a cylindrical head 8'b. The latter has a blind hole 8'c allowing the positioning either of a cylindrical rod 8'd provided at one of its ends with a spherical head 8'e, pivotably mounting the pedicular screw relative to the sleeve or with a cylindrical finger 8'f comprising at one of its ends a stop 8'g. The cylindrical rod 8'd and the finger 8'f are maintained inside each corresponding blind hole 8'c via a set screw 8'h or any other like means.

On the base 1b of the element 1' is placed an elastic body 3' such as a block of natural or synthetic rubber. The rod 8'd is introduced via the notch 1'd inside the hollow cylinder 1'a so that its spherical head 8'e comes into abutment against the elastic body 3'. Prior to the positioning of the rod 8'd, there is placed around the spherical head 8'e a sleeve or ring 8'i of which the inner and outer faces take the profile of a portion of sphere with the same diameter as that of the head 8'e. The ring 8'i is made of a material such as metal or TEFLON. Another elastic body 4' identical to the one referenced 3' is placed inside the hollow cylinder 1'a to come into abutment against the ring 8'i secured to the sphere 8'e. The end opposite that, 1'b, of the hollow cylinder 1'a is then closed by the disc 2' for its surface 2'c to abut against the elastic body 4'.

In place of ring 8'i, there may be provided a cup of the same profile which is placed on either side of the spherical head 8'e in order that the latter does not abut directly on the elastic bodies.

It will be noted that the cylindrical rod 8'd comprising the spherical head 8'e associated with its ring 8'i is mounted to pivot between two elastic bodies 3' and 4' in order to dampen its displacements when the vertebrae are subjected to efforts of traction/compression.

The elastic bodies 3' and 4' may for example present a conical profile of which the less wide base is in abutment respectively against the bottom 1'b of the element 1' and the surface 2'c of the disc 2'.

Depending on the number of discs to be relieved, the surgeon will proceed with different assemblies of the elements 1' such as for example those shown in FIGS. 6 and 7.

In fact, when one disc only is to be relieved, the surgeon will previously fix two screws 8' in each of the vertebrae lying above and below the disc. He introduces in the first screw 8', i.e. the one lying above the disc to be relieved, a rod 8'd secured to the element 1' so that the free end of the lug 2'a of the disc 2' and more particularly its hole 2'd cooperates with a certain clearance with the finger 8'f which is placed inside the second screw 8' disposed in the vertebra lying below the disc (FIG. 6). This particular assembly will thus make it possible, during displacement of the vertebrae, to relieve and dampen the efforts of compression and of traction to which the disc is subjected.

On the other hand, when several discs are to be relieved, the surgeon proceeds with the assembly as shown in FIG. 7. It is possible to mount a plurality of elements 1' one above the other so that each lug 2'a of the discs 2' cooperates with the rod 8'd of the element 1' lying directly therebelow. The first element 1' of the assembly abuts on a pedicular screw 8' associated with a finger 8'f secured to the stop 8'g as was described hereinabove in FIG. 6. Such assembly may be repeated for several levels to be relieved.

Figure 8:
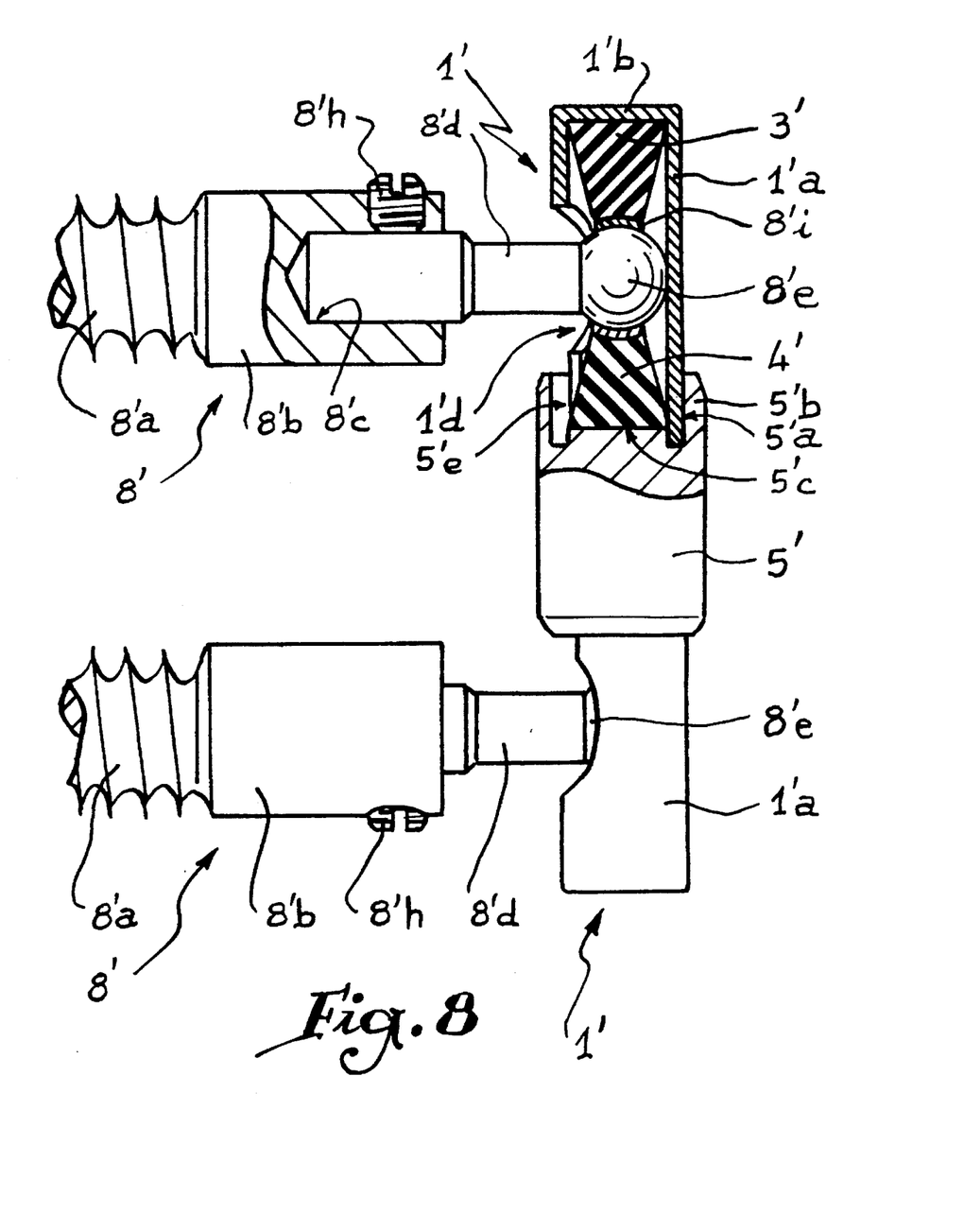
FIG. 8 is a view showing a variant assembly of the dampers shown in FIG. 6.

FIG. 8 shows a particular assembly of two identical elements 1' described hereinabove. Assembly is provided to relieve, for example, a disc located between two vertebrae of the spine. The two elements 1' are joined via a cylindrical sleeve 5'. The sleeve 5' is provided to replace the disc 2' described hereinbefore. The sleeve 5' comprises at each end a blind hole 5'a whose internal diameter is equivalent to the external diameter of the cylinder 1'a of each element 1' to be joined. In the bottom of each blind hole 5'a is provided a bearing surface 5'c identical to that, referenced 2'c and of diameter equivalent to the internal diameter of the cylinder 1'a so as to define a cylindrical notch 5'e for fixing the elements 1'. The blind hole 5'a a defines on its periphery a skirt 5'b which axially guides the cylinder 1'a and maintains it vertically. The bearing surface 5'c is provided to receive one of the ends of the elastic bodies 3' or 4' of each element 1' to be joined. Such assembly makes it possible, in the same manner as previously, to dampen the efforts of traction and compression in order to relieve the damaged discs.

Of course, a bellows which has not been shown but which is identical to those referenced 8, 90', surrounds the rod 8'd secured to the pedicular screws 8' in order to protect the internal part of the elements 1'.

Figure 9:
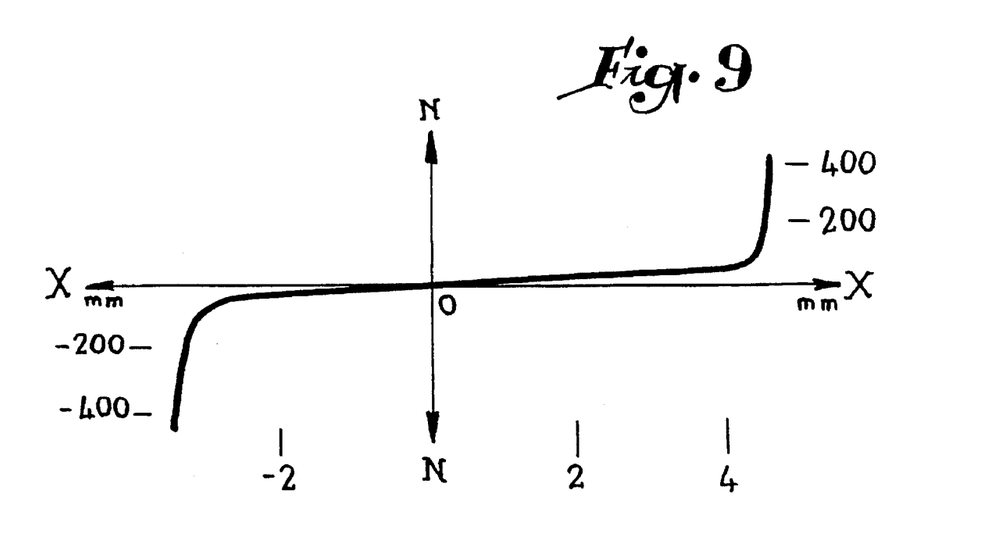
FIG. 9 is a curve showing the variations of the resistive force developed by the damper.

FIG. 9 shows the curve which illustrates the variation of the force of resistance of the damper according to the present invention. The left-hand part of the curve corresponds to an effort of compression applied on the damper and which in fact presents a negative displacement illustrated from the origin. The reaction N increases for the majority of the displacement in relatively slight manner, i.e. it is approximately tangential to the X-axis representing the displacement. It then becomes exponential and is finally asymptotic with respect to a straight line (not shown) parallel to the axis of the forces N.

If, on the contrary, the displacement of the damper is positive (case of a traction), the curve illustrating the antagonistic resistance of the damper is symmetrical with respect to that corresponding to a compression, this part of the curve becoming asymptotic with respect to a straight line (not shown), but likewise parallel to the axis of the positive forces N.

A regulation of the bending-stretching movement between two vertebrae is therefore obtained, developing a curve of the forces N and exponential displacements X in the two directions, which corresponds to the physiological course of the discal movement.

When the different prostheses described above are functioning, it is noticed that they define an amplitude of bending-stretching whose limits correspond to the vertical zones of the curve shown in FIG. 9. These vertical zones may be modified to control the sector of mobility in bending-stretching.

Of course, the curve is totally symmetrical if the elastic bodies 7 or 60, 70 or 60', 70' or 3', 4' present the same characteristics of volume and of flexibility and if the chambers which receive them are of the same volume. On the other hand, both the characteristics of the elastic blocks and the volumes of the chambers receiving them may be varied so as to obtain different resistances to compression or to traction.

It will be noted that the dampers described hereinabove may be superposed with respect to the spine thanks to pedicular screws comprising a plurality of spherical heads which are aligned along the major axis of and screw. It is observed that there is a link between each vertebra, which is totally stabilized, whether it be in traction or in compression via the damper. It is ascertained that the elastic bodies of each prosthesis described hereinabove may each be associated with a spring to improve their damping effort, and they may present any outer profile.

It will be noted that the dampers described create devices for intervertebral stabilization, but other medical applications may be envisaged. For example, such dampers may be used in combination with any system of prosthesis such as for example an osteosynthesis device in order to create a combination of a fixed rachidian zone whose ends are mechanically assisted and supple.

What is claimed is:

1. A damper for regulating the bending-stretching movement between the vertebrae spaced on either side of a disc the damper comprising: a pair of elements, each of said elements including a body, each of said bodies having opposite ends, an opening in each of said bodies intermediate said opposite ends, pivot means in each of said bodies communicating with each of said openings for pivotably mounting a pedicular screw to each of said bodies, at least one chamber within each of said bodies intermediate said pivot means and one of said opposite ends of said bodies, said at least one chamber defining a first volume, an elastic element mounted within said at least one chamber of each of said bodies and being engageable by said pivot means, each of said elastic elements normally defining a lesser volume than said first volume, and means for connecting said bodies in generally an end to end alignment.

2. The damper of claim 1 in which said one of said opposite ends of each of said bodies includes a bottom wall, a tenon extending outwardly of each of said bodies from said bottom wall, a disc means mounted to each of said bodies so as to close the other of said opposite ends of said bodies, a sleeve mounted within each of said bodies and having an opening aligned with said openings in said bodies, each of said sleeves having a bottom wall which engages said elastic element, said pivot means including a spherical head portion mounted within said sleeve and an outer portion extending through said opening of said body and said opening of said sleeve, and means for securing said outer portion to a pedicular screw.

3. The damper of claim 2 in which each of said disc means includes a tenon extending outwardly therefrom, said means for connecting said bodies including an assembly ring means having opposite ends, said opposite ends of the assembly ring means being engageable with said tenon extending from said bottom wall of one of said bodies and said tenon extending from said disc means of the other of said bodies.

4. The damper of claim 3 in which said assembly ring means includes a notch in each opposite end thereof for selectively receiving said tenon extending from said bottom wall of one of said bodies and said tenon extending from said disc means of the other of said bodies therein.

5. The damper of claim 2 in which each of said disc means includes a hollow base which is engageable with said spherical head of said pivot means.

6. The damper of claim 5 in which said bottom wall of said sleeve includes an internal profile having a radius complementary to the spherical head of said pivot means.

7. The damper of claim 2 in which said outer portion of each of said pivot means includes a threaded portion to which a pedicular screw may be mounted.

8. The damper of claim 7 in which said outer portion of each of said pivot means includes a generally cylindrical portion intermediate said threaded portion and said spherical head, and an opening through said cylindrical portion.

9. The damper of claim 1 including a sleeve means mounted within each of said bodies, said pivot means including a spherical head portion pivotably mounted within said sleeve means.

10. The damper of claim 9 in which said sleeve means includes a central bore having a radius complementary to the radius of said spherical head.

11. The damper of claim 9 in which said means for connecting each of said bodies includes a collar having oppositely oriented threaded portions, each of said bodies having threaded outer surfaces for complementarily receiving said threaded portions of said collar.

12. The damper of claim 9 in which each of said sleeve means includes a bore which is aligned with said opening in said bodies which communicates with an interior cavity of generally spherical configuration, said bores being of a size such that said spherical head of said pivot means are press-fitted into said cavities.

13. The damper of claim 12 in which said pivot means includes a pedicular screw means integrally formed with said spherical head.

14. The damper of claim 13 including a hexagonal profiled part formed between a threaded portion of said pedicular screw and said spherical head portion.

15. The damper of claim 9 including first and second chambers within each of said bodies intermediate said sleeve means and each of said opposite ends, each of said first and second chambers defining first and second volumes, first and second elastic elements mounted within each of said first and second chambers, respectively, each of said first and second elastic elements defining a volume which is smaller than said first and second chambers, respectively, each of said sleeve means being movable against each of said first and second elastic elements within said bodies thus reducing said first and second volumes and increasing the resistance of said first and second elastic elements to movement of said sleeve means.

16. The damper of claim 15 including a pair of aligned openings in opposite sides of said bodies, said sleeve means defining opposite openings aligned with said aligned openings in said body, each of said pivot means being a spherical element mounted within said sleeve means, pedicular screws having cylindrical portions extending through said spherical element, and means for securing said cylindrical portion of said pedicular screws within said spherical elements.

17. The damper of claim 15 in which said means for connecting said bodies together includes a disc portion for closing one of said ends of one of said bodies, a lug extending outwardly from said disc portion and generally parallel with respect to a longitudinal axis taken along said one of said bodies, said lug including an opening therein through which an outer portion of said pivot means of an adjacent element extends.

18. The damper of claim 17 in which said outer portion of said pivot means is received within a recess formed in a pedicular screw, and means for securing said pedicular screw to said outer portion.

19. The damper of claim 15 in which each of said first and second elastic elements are generally conically shaped having a base portion and a face portion which is narrower than said base portion and which is engaged with said sleeve means.

20. The damper of claim 9 in which said means for joining said first and second bodies includes a sleeve for connecting opposing ends of said bodies.

21. The damper of claim 20 wherein said sleeve includes opposite blind holes for receiving opposing elastic elements of said bodies.

22. The damper of claim 21 in which each of said pivot means includes an extension, a pedicular screw having a bore therein, said extension being receivable within said bore and means for securing said pedicular screw to said extension.

23. The damper of claim 1 in which each of said pivot means includes an outer portion extending through said opening, including a bellows surrounding each of said outer portion of said pivot means so as to close said openings in each of said bodies to prohibit the entrance of particles through said openings and into said bodies.

24. A damper for regulating the bending-stretching movement between two vertebrae spaced on either side of a disc, said damper comprising: a pair of elements, each of said elements including a cylindrical body having opposite ends, an opening in each of said bodies intermediate said opposite ends, sleeve means mounted within each of said bodies and defining an opening communicating with said openings in said bodies, pedicular screw means, said pedicular screw means including a head portion pivotably mounted within said sleeve means and having a portion extending outwardly through said openings in said body, at least one chamber within each of said bodies intermediate said sleeve means and one of said opposite ends thereof, said at least one chamber defining a first volume, an elastic element mounted within said at least one chamber and being engaged by said sleeve means so as to be compressible within said chamber, said elastic element normally defining a volume which is less than said first volume.

25. The damper of claim 24 including a second chamber between each said other end of said bodies and said sleeve means, said second chamber defining a second volume, a second elastic element mounted within said second chamber and engaged by said sleeve means, said second elastic element normally defining a volume which is less than said second volume.

* * * * *